(12) United States Patent
Smith

(10) Patent No.: US 12,721,635 B2
(45) Date of Patent: Sep. 1, 2026

(54) STEM IMPLANT REMOVAL TOOL

(71) Applicant: Zimmer, Inc., Warsaw, IN (US)

(72) Inventor: Aaron P. Smith, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 18/818,859

(22) Filed: Aug. 29, 2024

(65) Prior Publication Data

US 2025/0120729 A1 Apr. 17, 2025

Related U.S. Application Data

(60) Provisional application No. 63/590,643, filed on Oct. 16, 2023.

(51) Int. Cl.
*A61B 17/16* (2006.01)
*A61B 17/00* (2006.01)

(52) U.S. Cl.
CPC .. *A61B 17/1668* (2013.01); *A61B 2017/0046* (2013.01)

(58) Field of Classification Search
CPC ............... A61F 2/4607; A61B 17/1668; A61B 17/1604
See application file for complete search history.

(56) References Cited

U.S. PATENT DOCUMENTS 10,751,070 B2 8/2020 Pendleton et al.

*Primary Examiner* — Andrew Yang
(74) *Attorney, Agent, or Firm* — SCHWEGMAN LUNDBERG & WOESSNER, P.A.

(57) ABSTRACT

A tool for removing a stem implant that has been implanted within a bone can include a cutting section and a clearance section. The cutting section can extend from a proximal portion to a distal portion. The cutting section can include a blade configured to generally conform to an exterior geometry of the stem implant. The clearance section can be disposed adjacent to the cutting section such that a distal portion of the clearance section can be joined to the proximal portion of the cutting section. A proximal portion of the clearance section can be configured to receive and transmit forces to drive the cutting section along a desired trajectory for removal of the stem implant. The clearance section can be shaped to provide an offset that prevents interference with a neck of the stem implant while the cutting section is being driven along a desired trajectory.

20 Claims, 8 Drawing Sheets

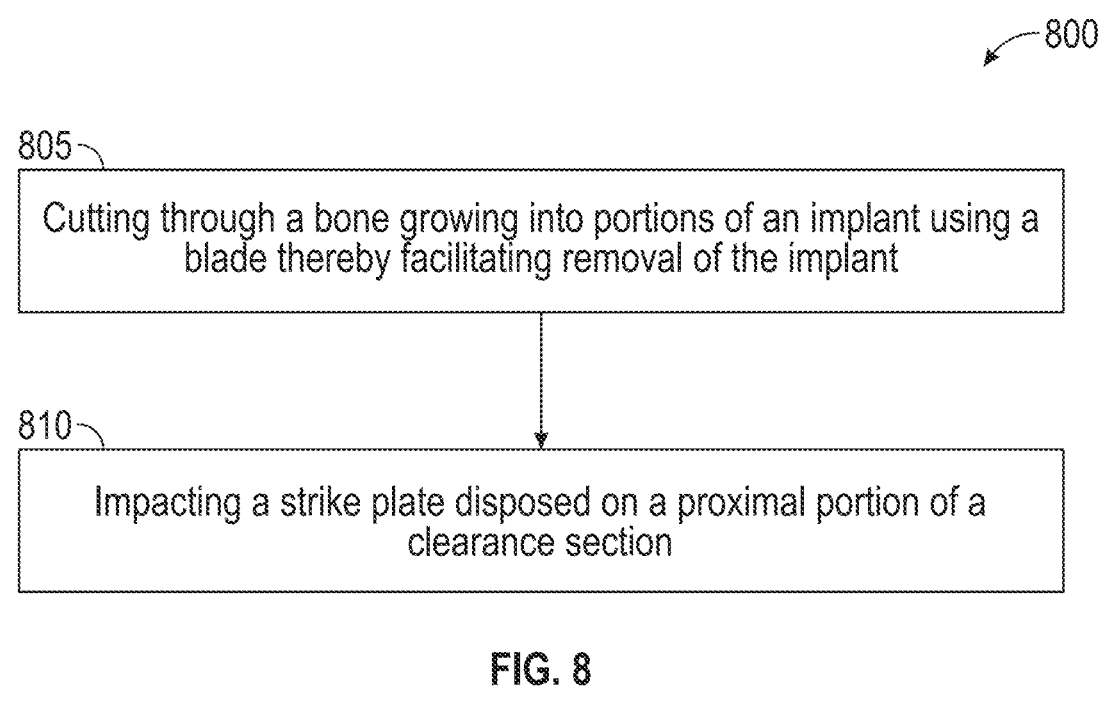

800

805

Cutting through a bone growing into portions of an implant using a blade thereby facilitating removal of the implant

810

Impacting a strike plate disposed on a proximal portion of a clearance section

FIG. 8

STEM IMPLANT REMOVAL TOOL

CLAIM OF PRIORITY

This application claims the benefit of U.S. Provisional Patent Application Ser. No. 63/590,643, filed on Oct. 16, 2023, the benefit of priority of which is claimed hereby, and which is incorporated by reference herein in its entirety.

TECHNICAL FIELD

Examples described herein generally relate to medical tools and, more specifically, medical tools for removing a stem implant.

BACKGROUND

Implants such as hip and knee replacements often utilize a stem that is inserted into the bone to anchor the implant. Over time, these stem implants may need to be replaced due to wear, breakage, or other issues. Removing a stem implant that has been in place for an extended period poses challenges, as bone tends to grow into and tightly integrate with the implant.

Current techniques for removing stem implants can be difficult and invasive. Extended surgical time is often required to carefully cut away and extract the implant from the surrounding bone growth. Accessing the deeply implanted stem poses difficulties, and care must be taken to avoid damaging healthy bone tissue during removal. Improper techniques risk leaving fragments of the implant behind or causing unnecessary harm to the bone.

Therefore, improved tools and techniques are needed to remove stem implants in a controlled and efficient manner while protecting the surrounding bone. Ideal solutions would allow a surgeon to detach the implant quickly and safely from ingrown bone and withdraw it fully intact with minimal bone loss. Such improvements would benefit both surgeon and patient by reducing surgical trauma, shortening procedure time, improving outcomes, and speeding recovery.

SUMMARY

In examples, a tool for removing a stem implant that has been implanted within a bone can include a cutting section, a handle section, and a clearance section. The cutting section can extend from a proximal portion to a distal portion. The cutting section can include a blade configured to generally conform to an exterior geometry of the stem implant. The handle section can extend from a proximal portion to a distal portion. The proximal portion can be configured to receive and transmit forces to drive the cutting section along a desired trajectory for removal of the stem implant. The clearance section can be disposed between the cutting section and the handle section such that a proximal portion of the clearance section is joined to the distal portion of the handle section and a distal portion of the clearance section is joined to the proximal portion of the cutting section. The clearance section can be shaped to provide an offset that prevents interference with a neck of the stem implant while the cutting section is being driven along the desired trajectory.

In examples, a tool for removing a stem implant that has been implanted within a bone can include a cutting section and a clearance section. The cutting section can extend from a proximal portion to a distal portion. The cutting section can include a blade configured to generally conform to an exterior geometry of the stem implant. The clearance section can be disposed adjacent to the cutting section such that a distal portion of the clearance section can be joined to the proximal portion of the cutting section. A proximal portion of the clearance section can be configured to receive and transmit forces to drive the cutting section along a desired trajectory for removal of the stem implant. The clearance section can be shaped to provide an offset that prevents interference with a neck of the stem implant while the cutting section is being driven along a desired trajectory.

In examples, a method of removing a stem implant from a femur using a tool for removing a stemmed implant from a bone can include cutting through femoral bone and/or tissue that is growing into portions of the stem implant using the blade thereby facilitating removal of the stem implant.

BRIEF DESCRIPTION OF THE DRAWINGS

Various examples are illustrated in the figures of the accompanying drawings. Such examples are demonstrative and not intended to be exhaustive or exclusive examples of the present subject matter.

FIG. 8 illustrates a flow diagram of an example of a method for removing an implant using an example tool.

DETAILED DESCRIPTION

Figure 1:
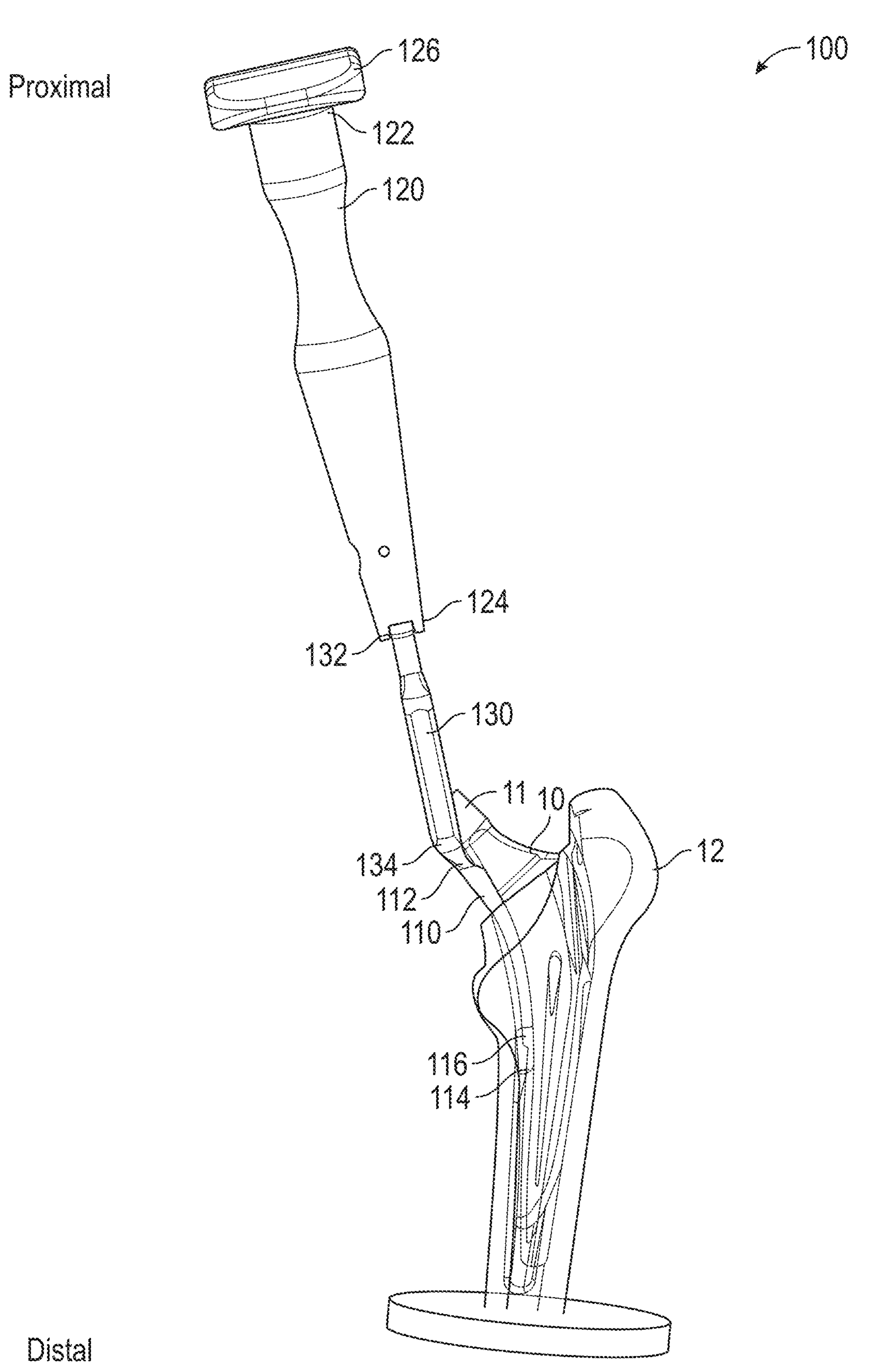
FIG. 1 illustrates an isometric view of an example of a tool for removing an implant.

FIG. 1 illustrates an isometric view of an example of a tool 100. The tool 100 can be for removing an implant 10 installed within a bone 12 of a patient. In examples, the implant 10 can be a stemmed implant or a stemless implant. In examples, the bone 12 can be a femur, humerus, hip bone, any other bone that can receive a stemmed implant or stemless implant, or the like. Thus, the tool 100 can be configured to remove any version of the implant 10 from any of the bone 12. The tool 100 can include a cutting section 110, a handle section 120, and a clearance section 130. FIG. 1 also includes markings for Distal and Proximal, which are labeled relevant to the tool and not the bone of the patient.

The cutting section 110 can be configured to engage with the implant 10 or the bone 12 to cut the bone 12 that has grown around and into the implant 10. The cutting section 110 can extend from a first portion 112 to a second portion 114. The cutting section 110 can include a blade 116. The blade 116 can be configured to generally conform to an exterior geometry of the implant 10. For example, the blade 116 can generally conform around a stem of a stemmed version of the implant 10.

The handle section 120 can be confirmed to be engaged with or held by a medical professional during the use of the tool 100. The handle section 120 can extend between a first portion 122 and a second portion 124. The first portion 122 can be configured to receive and transmit forces to drive the cutting section 110 along a desired trajectory for removal of the implant 10 from the bone 12.

As shown in FIG. 1, the first portion 122 of the handle section 120 can include a strike plate 126. The strike plate can be configured to be impacted by the medical professional with a hammer, mallet, a hand or other body part, or an energy-powered impactor or hammer to provide a force that drives the tool 100 along the desired trajectory to remove the implant 10 from the bone 12.

The clearance section 130 can be configured to prevent undesirable engagement between the tool 100 and the implant 10 or the bone 12. The clearance section 130 can be disposed between the cutting section 110 and the handle section 120. A first portion 132 of the clearance section 130 can be joined to the second portion 124 of the handle section 120 and a second portion 134 of the clearance section 130 can be joined to the first portion 112 of the cutting section 110. The clearance section 130 can be shaped to provide an offset that prevents interference with a neck 11 of the implant 10, or any unintended portions of the bone 12, while the tool 100 is being driven along the desired trajectory to remove the implant 10 from the bone 12. In examples, the clearance section 130 can include a concave profile, which can be configured to provide clearance between the clearance section 130 and the neck 11 of the implant 10 to prevent engagement between the clearance section 130 or the handle section 120 and the implant 10.

Figure 2:
FIG. 2 illustrates an isometric view of an example of a tool for removing an implant.
Figure 2:
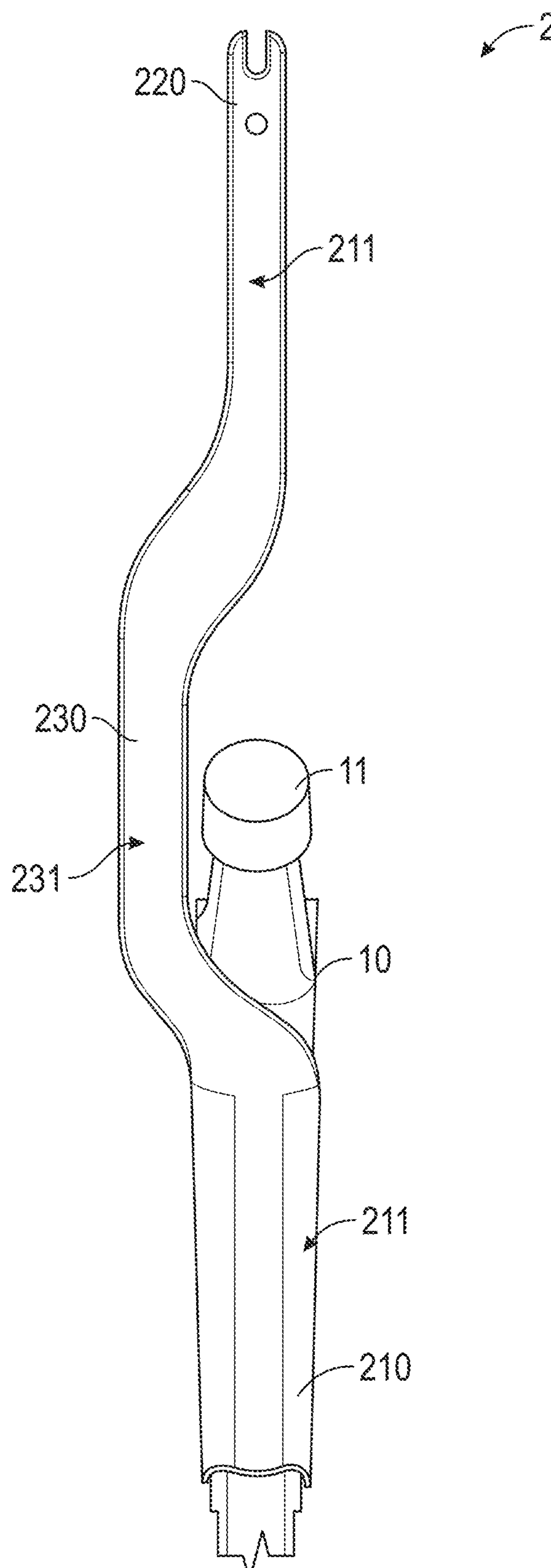

FIG. 2 illustrates an isometric view of an example of a tool 200 (e.g., the tool 100 (FIG. 1), or the like) for removing the implant 10 from the bone 12 of a patient. Like, the tool 100, the tool 200 can be configured to remove the implant 10 from the patient 12 while limiting unintended contact between the tool 200 and the implant 10 or the bone 12. FIG. 2 also includes markings for Distal and Proximal, which are labeled relevant to the tool and not the bone of the patient.

As shown in FIG. 2, the cutting section 210 and the handle section 220 can be longitudinally aligned. Additionally, the clearance section 230 can be longitudinally misaligned with the cutting section 210 and the handle section 220. The alignment of the cutting section 210 and the handle section 220 can help a medical professional guide, control, or align the tool 200 along a desired trajectory while removing the implant 10 from the bone 12. The misalignment between the clearance section 230 and each of the cutting section 210 and the handle section 220 can provide clearance between the tool 200 and the neck 11 of the implant 10 and the bone 12 during the removal of the implant 10 from the bone 12.

As shown in FIG. 2, the tool 200 can be aligned such that there are no twists between any of the cutting section 210, the handle section 220, or the clearance section 230 such that a major surface 211 of the cutting section 210, a major surface 221 of the handle section 220, and a major surface 231 of the clearance section 230 can generally face a same direction (as shown in FIG. 2, each of the major surface 211, the major surface 221, and the major surface 231 can face out of (or into) the page. As described herein, a major surface(s) is a surface(s) that has a largest surface area as compared to other surfaces of the same section or part.

Figure 3:
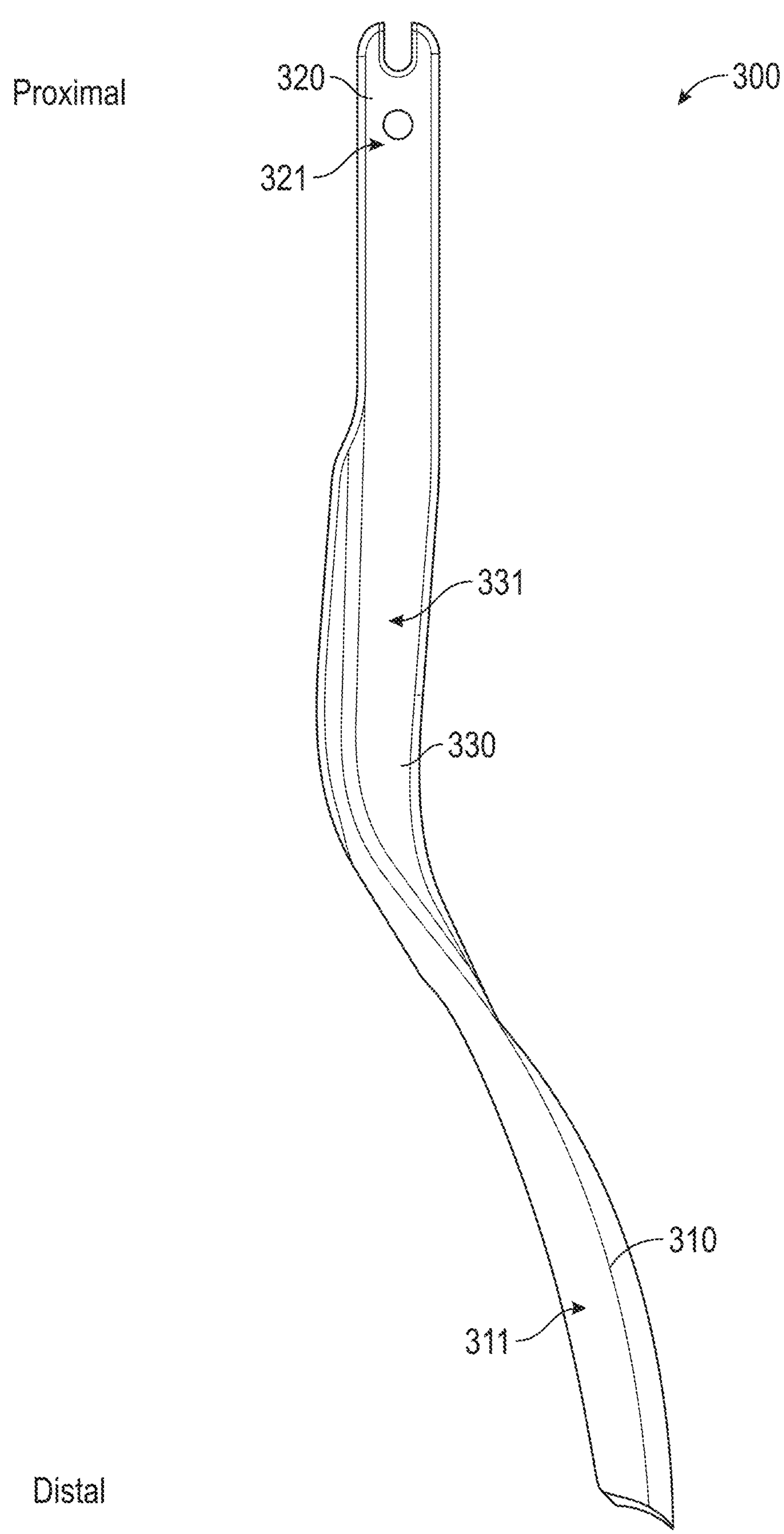
FIG. 3 illustrates an isometric view of an example of a tool for removing an implant.

FIG. 3 illustrates an isometric view of an example of a tool 300 (e.g., the tool 100 (FIG. 1), the tool 200 (FIG. 2), or the like) for removing the implant 10 from the bone 12 of a patient. Like, the tool 100 and the tool 200, the tool 300 can be configured to remove the implant 10 from the patient 12 while limiting unintended contact between the tool 300 and the implant 10 or the bone 12. FIG. 3 also includes markings for Distal and Proximal, which are labeled relevant to the tool and not the bone of the patient.

As shown in FIG. 3, the cutting section 310 can be longitudinally misaligned with the handle section 320 and the clearance section 330 of the tool 300. Additionally, the handle section 320 and the clearance section 330 can be longitudinally aligned. The alignment of the handle section 320 and the clearance section 330 and the misalignment of the cutting section 310 and each of the handle section 320 and the clearance section 330 can provide clearance between the tool 300 and the neck 11 of the implant 10 or unintended portions of the bone 12 while providing a better viewing window of the cutting section 310 engaging with the implant 10 and the bone 12 during the medical procedure.

As shown in FIG. 3, the tool 300 can be misaligned such that there is one or more twists between any of the cutting section 310, the handle section 320, or the clearance section 330 such that a major surface 311 of the cutting section 310, a major surface 321 of the handle section 320, and a major surface 331 of the clearance section 330 can generally face a different direction (as shown in FIG. 3, the major surface 211 generally faces toward a left or right direction in the figure, and the major surface 221, and the major surface 231 can face out of (or into) the page. In examples, each of the major surface 211, the major surface 221, and the major surface 231 can face in different directions such that none of the major surface 211, the major surface 221, or the major surface 231 are aligned.

Figure 4:
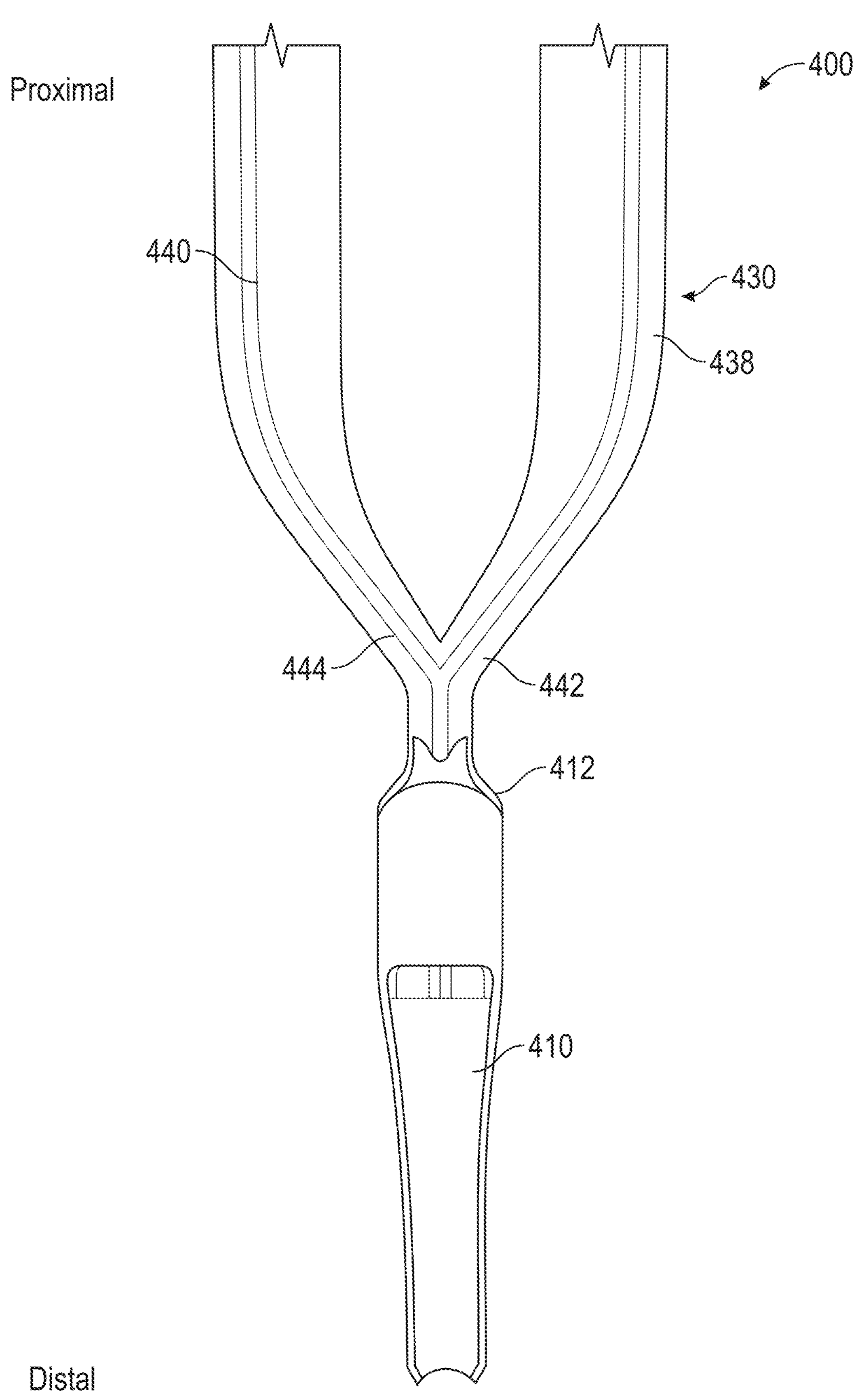
FIG. 4 illustrates an isometric view of an example of a tool for removing an implant including a U-shaped bifurcation in a clearance section.

FIG. 4 illustrates an isometric view of an example of a tool 400 (e.g., the tool 100 (FIG. 1), the tool 200 (FIG. 2), the tool 300 (FIG. 3), or the like) for removing an implant 10 from the bone 12 of a patient. Like, the tool 100, the tool 200, or the tool 300, the tool 400 can be configured to remove the implant 10 from the patient 12 while limiting unintended contact between the tool 400 and the implant 10 or the bone 12. As shown in FIG. 4, the clearance section 430 of the tool 400 can include a first portion 438 and a second portion 440. FIG. 4 also includes markings for Distal and Proximal, which are labeled relevant to the tool and not the bone of the patient.

In examples, a distal end 442 of the first portion 438 and a distal end 444 of the second portion 440 can converge to connect to the proximal portion 412 of the cutting portion 410. From the distal end and toward the proximal end of the first portion 438 the second portion 440 can diverge such that the first portion 438 and the second portion 440 include a U-shaped profile.

The proximal end of the first portion 438 and the proximal end of the second portion 440 can each be attached to the handle portion (e.g., the handle section 120 (FIG. 1), the handle section 220 (FIG. 2), or the handle section 320 (FIG. 3)) of the tool 400. In examples, a strike plate (e.g., the strike plate 126 (FIG. 1)) can be attached to either, or both, of the proximal end of the first portion 438 and the proximal end of the second portion 440. In examples, each of the proximal end of the first portion 438 and the proximal end of the second portion 440 can include an attachment mechanism that can permit attachment to the proximal end of the first portion 438 and the proximal end of the second portion 440 and a powered impactor, tool, specialized strike plate, or the like to aid in the use of the tool 400.

In examples, the proximal end of the first portion 438 and the proximal end of the second portion 440 can form the handle portion. For example, the proximal end of the first portion 438 and the proximal end 448 of the second portion can include a striking surface or a handle surface that can help a medical professional guide and operate the tool 400.

Figure 5:
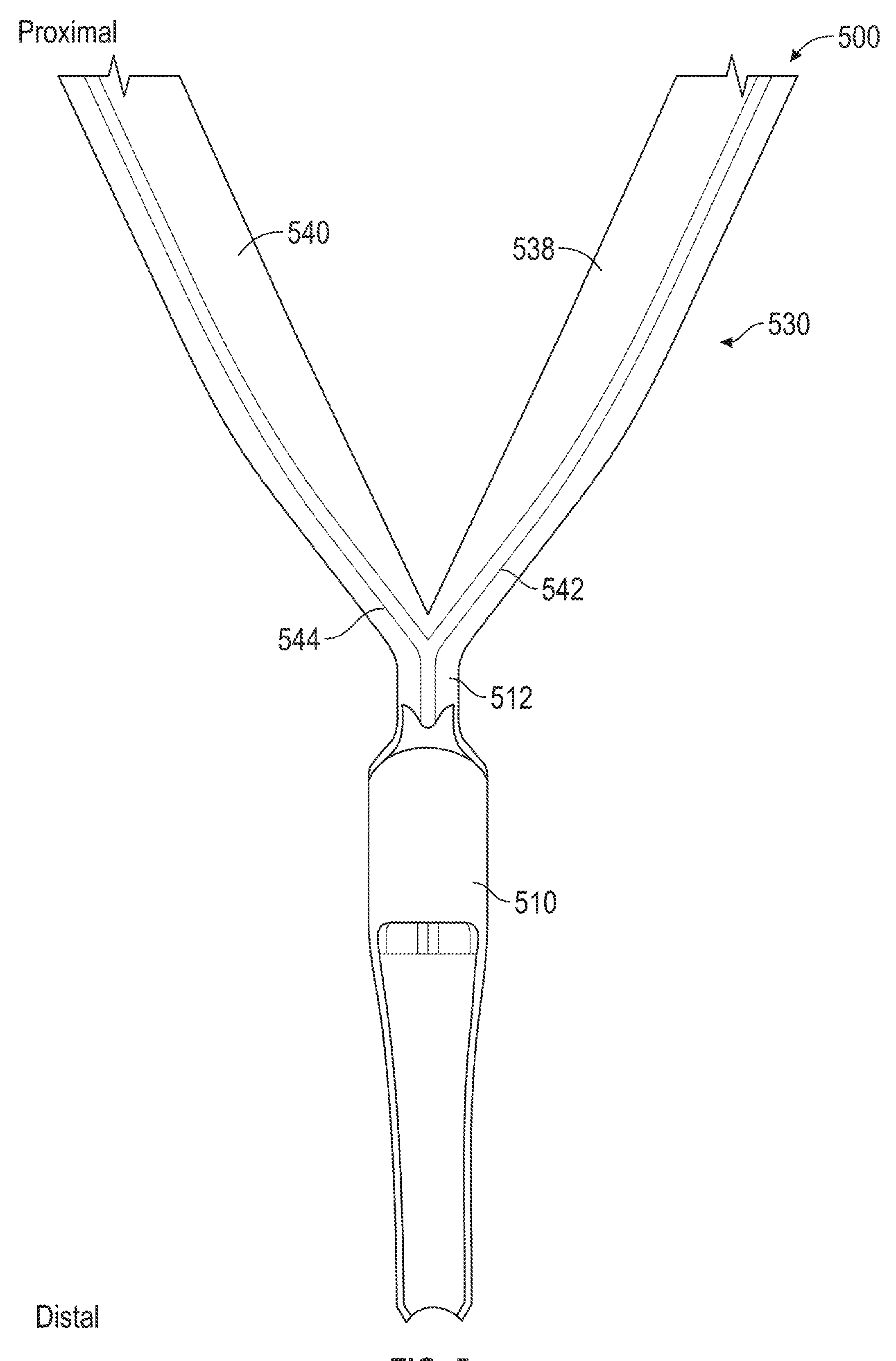
FIG. 5 illustrates an isometric view of an example of a tool for removing an implant including a V-shaped bifurcation in a clearance section.

FIG. 5 illustrates an isometric view of an example of a tool 500 (e.g., the tool 100 (FIG. 1), the tool 200 (FIG. 2), the tool 300 (FIG. 3), the tool 400 (FIG. 4), or the like) for removing the implant 10 from the bone 12 of a patient. Like, the tool 100, the tool 200, the tool 300, or the tool 400, the tool 500 can be configured to remove the implant 10 from the patient 12 while limiting unintended contact between the tool 500 and the implant 10 (FIG. 1) or the bone 12 (FIG. 1). As shown in FIG. 5, the clearance section 530 of the tool 500 can include a first portion 538 and a second portion 540. FIG. 5 also includes markings for Distal and Proximal, which are labeled relevant to the tool and not the bone of the patient.

In examples, a distal end 542 of the first portion 538 and a distal end 544 of the second portion 540 can converge to connect to the proximal portion 512 of the cutting portion 510. The first portion 538 and the second portion 540 can diverge as the first portion 538 and the second portion 540 extend away from the distal end 542 and the distal end 544, respectively, such that the first portion 538 and the second portion 540 include a V-shaped profile.

The proximal end of the first portion 538 and the proximal end of the second portion 540 can each be attached to the handle portion (e.g., the handle section 120 (FIG. 1), the handle section 220 (FIG. 2), and the handle section 320 (FIG. 3)) of the tool 500. In examples, a strike plate (e.g., the strike plate 126 (FIG. 1)) can be attached to either, or both, of the proximal end of the first portion 538 and the proximal end of the second portion 540. In examples, each of the proximal end of the first portion 538 and the proximal end of the second portion 540 can include an attachment mechanism that can permit attachment to the proximal end of the first portion 538 and the proximal end of the second portion 540 and a powered impactor, tool, specialized strike plate, or the like to aid in the use of the tool 500.

In examples, the proximal end of the first portion 538 and the proximal end of the second portion 540 can form the handle portion 520. For example, the proximal end of the first portion 538 and the proximal end of the second portion 540 can include a striking surface or a handle surface that can help a medical professional guide and operate the tool 500.

Figure 6:
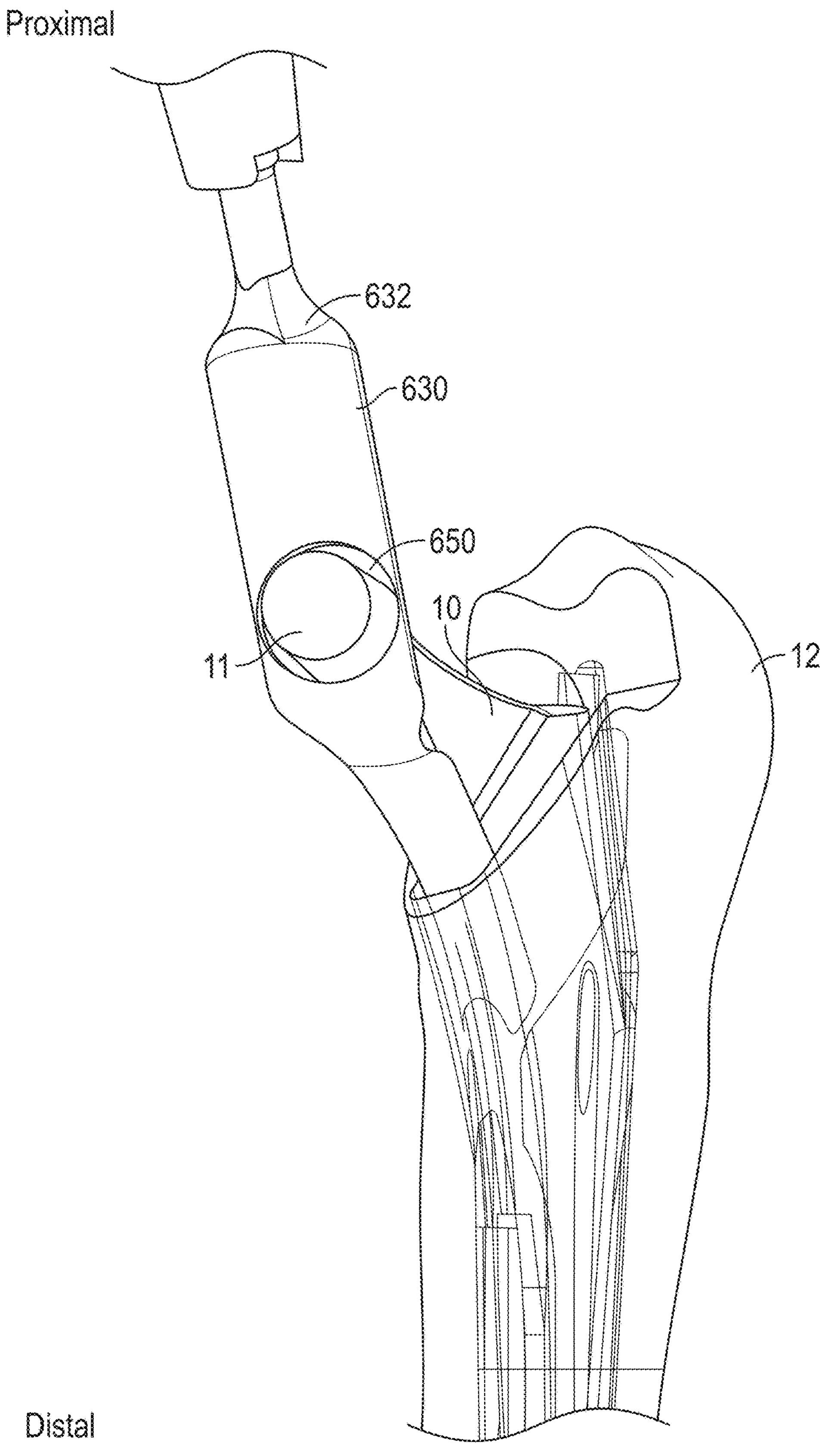
FIG. 6 illustrates an isometric view of an example of a tool for removing an implant including an aperture in a clearance section.

FIG. 6 illustrates an isometric view of an example of a tool 600 (e.g., the tool 100 (FIG. 1), the tool 200 (FIG. 2), the tool 300 (FIG. 3), the tool 400 (FIG. 4), the tool 500 (FIG. 5), or the like) for removing the implant 10 from a bone 12 of the patient. Like, the tool 100, the tool 200, the tool 300, the tool 400, and the tool 500, the tool 600 can be configured to remove the implant 10 from the patient 12 while limiting unintended contact between the tool 600 and the implant 10 or the bone 12. As shown in FIG. 6, the clearance portion 630 of the tool 600 can include a first aperture 650. FIG. 6 also includes markings for Distal and Proximal, which are labeled relevant to the tool and not the bone of the patient.

The first aperture 650 can be configured to provide clearance between the clearance portion 630 and the implant 10 or the bone 12, which can help prevent unintended contact between the tool 600 and the implant 10 or the bone 12. For example, the first aperture 650 can be configured to receive the neck 11 of the implant 10 such that the neck 11 can extend through the first aperture 650 without other portions of the clearance portion 630 contacting the neck 11, or the implant 10.

In examples, the first aperture 650 can be formed in the clearance portion 630 as a perfect circular cutout. In another example, the first aperture 650 can be cut out of the clearance portion 630 to perfectly contour to the neck 11. For example, the first aperture 650 can be an ellipse, rectangle, triangle, square, or any other shape that can receive the neck 11 while avoiding contact between the clearance portion 630 and the rest of the tool 100. In yet another example, the clearance portion 630 can include more than one aperture. Here, the clearance portion 630 can include the first aperture 650 with one or more apertures spaced along the clearance portion 630 toward the proximal portion 632. The series of apertures can provide multiple angles that the tool 600 can be used to remove the implant 10 from the bone 12, while giving the medical professional more options and techniques to successfully cut the bone 12 away from the implant 10 than other options without an aperture or with just one aperture.

Figure 7:
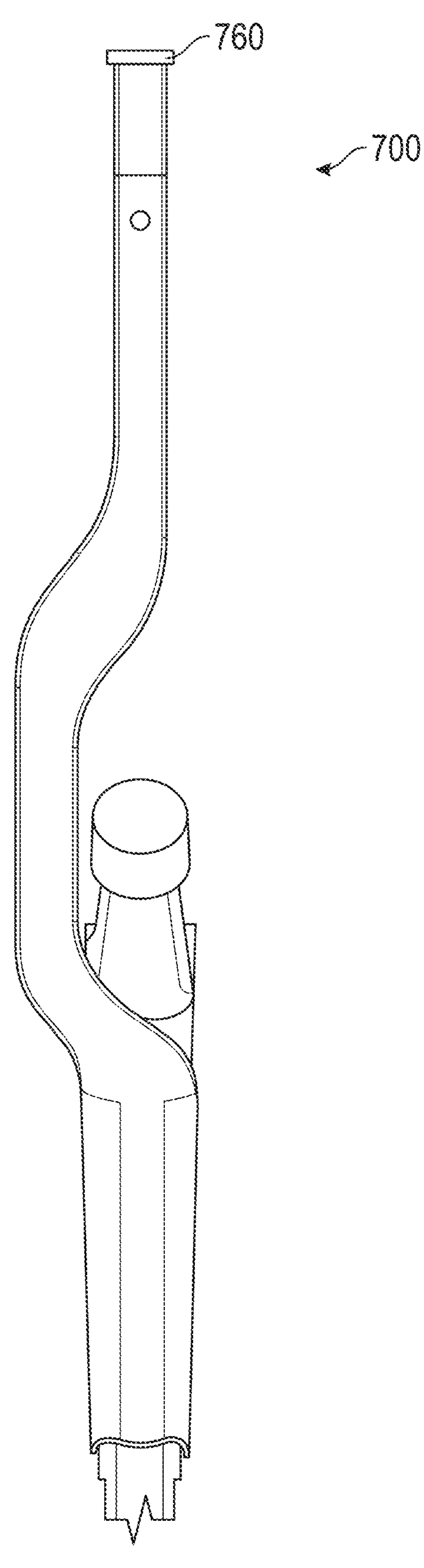
FIG. 7 illustrates an isometric view of an example of a tool for removing an implant including an attachment portion.

FIG. 7 illustrates an isometric view of an example of a tool 700 (e.g., the tool 100 (FIG. 1), the tool 200 (FIG. 2), the tool 300 (FIG. 3), the tool 400 (FIG. 4), the tool 500 (FIG. 5), the tool 600 (FIG. 6), or the like) for removing the implant 10 from the bone 12 of the patient. Like, the tool 100, the tool 200, the tool 300, the tool 400, the tool 500, and the tool 600, the tool 700 can be configured to remove the implant 10 from the bone 12 while decreasing or minimizing undesired contact between the tool 700 and the implant 10 or the bone 12. As shown in FIG. 7, the tool 700 can include an attachment mechanism 760. FIG. 7 also includes markings for Distal and Proximal, which are labeled relevant to the tool and not the bone of the patient.

The attachment mechanism 760 can be configured to attach one or more engagement devices (e.g., energy-powered tools (e.g., a power impactor, power hammer, or the like), strike plates (e.g., the strike plate 126 (FIG. 1)), surgical robots, or the like) to the tool 700. As such, the attachment mechanism 760 can enable the tool 700 to be used with human force (when the strike plate is installed thereon), with energy power (when the energy-powered tool is on), or with automation (when the surgical robot is installed). Though the attachment mechanism 760 is only shown on the tool 700, the attachment mechanism 760 can be attached to any of the tools 100-600 (shown in FIGS. 1-6, respectively).

FIG. 8 illustrates a schematic view of the method 800, in accordance with at least one example of this disclosure. The method 800 can be a method of removing an implant (e.g., the implant 10 (FIG. 1)) from a bone (e.g., the bone 12 (FIG. 1)) using an example tool (e.g., any of tools 100-700 (FIGS. 1-7, respectively).

At operation 805, the method 800 can include cutting through femur (e.g., the bone 12), other bones, or tissue surrounding the implant that is growing into portions of the stem implant (e.g., the implant 10) using the blade (e.g., the cutting section of any of the tools 100-700) thereby facilitating removal of the stem implant (e.g., the bone 12 (FIG. 1)).

At operation 810, the method 800 can include impacting a strike plate (e.g., the strike plate 126 (FIG. 1)) disposed on the proximal portion of the clearance section. As discussed herein, the tool can be operated using a hammer or a mallet on the strike plate, an energy-powered tool, or a surgical robot. As such, the tool's design can improve the effectiveness of the tool by allowing better access to the implant within the bone while helping limit interference between the tool and parts of the implant or bone that are not intended to be contacted by the medical professional.

The following, non-limiting examples, detail certain aspects of the present subject matter to solve the challenges and provide the benefits discussed herein, among others.

Example 1 is a tool for removing a stem implant that has been implanted within a bone, comprising: a cutting section extending from a proximal portion to a distal portion, the cutting section including a blade configured to generally conform to an exterior geometry of the stem implant; a handle section extending from a proximal portion to a distal portion, the proximal portion configured to receive and transmit forces to drive the cutting section along a desired trajectory for removal of the stem implant; and a clearance section disposed between the cutting section and the handle section such that a proximal portion of the clearance section is joined to the distal portion of the handle section and a distal portion of the clearance section is joined to the proximal portion of the cutting section, the clearance section shaped to provide an offset that prevents interference with a neck of the stem implant while the cutting section is being driven along the desired trajectory.

In Example 2, the subject matter of Example 1 includes, wherein the proximal portion of the handle section comprises a connector for attachment to a powered impactor.

In Example 3, the subject matter of Examples 1-2 includes, wherein the proximal portion of the handle section comprises a strike plate.

In Example 4, the subject matter of Examples 1-3 includes, wherein the proximal portion of the handle section comprises a connector for attachment to a surgical robot.

In Example 5, the subject matter of Examples 1~4 includes, wherein the cutting section is longitudinally aligned with the handle section, and wherein the clearance section is longitudinally misaligned with the cutting section and the clearance section.

In Example 6, the subject matter of Examples 1-5 includes, wherein the clearance section includes a first portion and a second portion, wherein a distal end of the first portion and a distal end of a second portion converge and connect to the cutting section, and wherein a proximal end of the first portion and the second portion diverge such that the first portion and the second portion form a U-shaped profile.

In Example 7, the subject matter of Example 6 includes, wherein the handle section is disposed on the proximal end of each of the first portion and the second portion, and wherein the handle section includes a strike plate.

In Example 8, the subject matter of Examples 1-7 includes, wherein the clearance section includes a first portion and a second portion, wherein a distal end of the first portion and a distal end of a second portion converge and connect to the cutting section, and wherein a proximal end of the first portion and the second portion diverge such that the first portion and the second portion form a V-shaped profile.

In Example 9, the subject matter of Example 8 includes, wherein the handle section is disposed on the proximal end of each of the first portion and the second portion, and wherein the handle section includes a strike plate.

In Example 10, the subject matter of Examples 1-9 includes, wherein the clearance section comprises a first aperture configured to provide clearance between the clearance section and the stem implant to prevent engagement between the clearance section or the handle section and the stem implant.

In Example 11, the subject matter of Examples 1-10 includes, wherein the clearance section comprises a concave profile, the concave profile configured to provide clearance between the clearance section and the stem implant to prevent engagement between the clearance section or the handle section and the stem implant.

Example 12 is a tool for removing a stem implant that has been implanted within a bone, comprising: a cutting section extending from a proximal portion to a distal portion, the cutting section including a blade configured to generally conform to an exterior geometry of the stem implant; and a clearance section disposed adjacent to the cutting section such that a distal portion of the clearance section is joined to the proximal portion of the cutting section, a proximal portion of the clearance section configured to receive and transmit forces to drive the cutting section along a desired trajectory for removal of the stem implant, the clearance section shaped to provide an offset that prevents interference with a neck of the stem implant while the cutting section is being driven along a desired trajectory.

In Example 13, the subject matter of Example 12 includes, wherein the clearance section includes a first portion and a second portion, wherein a distal end of the first portion and a distal end of a second portion converge and connect to the cutting section, and wherein a proximal end of the first portion and the second portion diverge such that the first portion and the second portion form a U-shaped profile.

In Example 14, the subject matter of Example 13 includes, wherein a handle section is disposed on the proximal end of each of the first portion and the second portion, the handle section extending from a proximal portion to a distal portion, the proximal portion of the handle section configured to receive and transmit forces to drive the cutting section along a desired trajectory for removal of the stem implant, and wherein the handle section includes a strike plate.

In Example 15, the subject matter of Examples 12-14 includes, wherein the clearance section includes a first portion and a second portion, wherein a distal end of the first portion and a distal end of a second portion converge and connect to the cutting section, and wherein a proximal end of the first portion and the second portion diverge such that the first portion and the second portion form a V-shaped profile.

In Example 16, the subject matter of Example 15 includes, wherein a handle section is disposed on the proximal end of each of the first portion and the second portion, the handle section extending from a proximal portion to a distal portion, the proximal portion of the handle section configured to receive and transmit forces to drive the cutting section along a desired trajectory for removal of the stem implant, and wherein the handle section includes a strike plate.

In Example 17, the subject matter of Examples 12-16 includes, wherein the clearance section comprises a first aperture configured to provide clearance between the clearance section and the stem implant to prevent engagement between the clearance section and the stem implant.

In Example 18, the subject matter of Examples 12-17 includes, wherein the clearance section comprises a concave profile, the concave profile configured to provide clearance between the clearance section and the stem implant to prevent engagement between the clearance section and the stem implant.

Example 19 is a method of removing a stem implant from a femur using the tool of Example 12, the method comprising: cutting through femur growing into portions of the stem implant using the blade thereby facilitating removal of the stem implant.

In Example 20, the subject matter of Example 19 includes, wherein cutting through femur growing into portions of the stem implant using the blade, comprises: impacting a strike plate disposed on the proximal portion of the clearance section.

Example 21 is an apparatus comprising means to implement any of Examples 1-20.

Example 22 is a system to implement any of Examples 1-20.

Example 23 is a method to implement any of Examples 1-20.

Example 24 is an apparatus, system, or method including elements of any of any of Examples 1-20.

The above detailed description includes references to the accompanying drawings, which form a part of the detailed description. The drawings show, by way of illustration, specific examples that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5). Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The above description is intended to be illustrative, and not restrictive. For example, the above-described examples (or one or more aspects thereof) may be used in combination with each other. Other examples may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the examples should be determined with reference to the appended claims, along with the full scope of equivalents to which such claims are entitled.

The invention claimed is:

1. A tool for removing a stem implant that has been implanted within a bone, comprising:

a cutting section extending from a proximal portion to a distal portion, the cutting section including a blade configured to generally conform to an exterior geometry of the stem implant;

a handle section extending from a proximal portion to a distal portion, the proximal portion configured to receive and transmit forces to drive the cutting section along a desired trajectory for removal of the stem implant; and a clearance section disposed between the cutting section and the handle section such that a proximal portion of the clearance section is joined to the distal portion of the handle section and a distal portion of the clearance section is joined to the proximal portion of the cutting section, the clearance section shaped to provide an offset that prevents interference with a neck of the stem implant while the cutting section is being driven along the desired trajectory;

wherein the cutting section and the handle section are rotationally offset from one another such that a major surface of the cutting section faces a different direction than a major surface of the handle section;

wherein the major surface of the cutting section includes a concave profile and the major surface of the handle section includes a planar profile; and wherein the clearance section transitions from the concave profile to the planar profile.

2. The tool of claim 1, wherein the proximal portion of the handle section comprises a connector for attachment to a powered impactor.

3. The tool of claim 1, wherein the proximal portion of the handle section comprises a strike plate.

4. The tool of claim 1, wherein the proximal portion of the handle section comprises a connector for attachment to a surgical robot.

5. The tool of claim 1, wherein the cutting section and the handle section are longitudinally aligned along a common longitudinal axis, and wherein the clearance section is longitudinally offset from the common longitudinal axis such that the clearance section is laterally displaced from both the cutting section and the handle section.

6. The tool of claim 1, wherein the clearance section includes a first portion and a second portion, wherein a distal end of the first portion and a distal end of the second portion converge and connect to the cutting section, and wherein a proximal end of the first portion and the second portion diverge such that the first portion and the second portion form a U-shaped profile.

7. The tool of claim 6, wherein the handle section is disposed on the proximal end of each of the first portion and the second portion, and wherein the handle section includes a strike plate.

8. The tool of claim 1, wherein the clearance section includes a first portion and a second portion, wherein a distal end of the first portion and a distal end of the second portion converge and connect to the cutting section, and wherein a proximal end of the first portion and the second portion diverge such that the first portion and the second portion form a V-shaped profile.

9. The tool of claim 8, wherein the handle section is disposed on the proximal end of each of the first portion and the second portion, and wherein the handle section includes a strike plate.

10. The tool of claim 1, wherein the clearance section comprises a first aperture configured to provide clearance between the clearance section and the stem implant to prevent engagement between the clearance section or the handle section and the stem implant.

11. The tool of claim 1, wherein the clearance section comprises a concave profile, the concave profile configured to provide clearance between the clearance section and the stem implant to prevent engagement between the clearance section or the handle section and the stem implant.

12. A tool for removing a stem implant that has been implanted within a bone, comprising:

a cutting section extending along a longitudinal axis from a proximal portion to a distal portion, the cutting section including a blade configured to generally conform to an exterior geometry of the stem implant; and a clearance section disposed adjacent to the cutting section such that a distal portion of the clearance section is joined to the proximal portion of the cutting section, a proximal portion of the clearance section configured to receive and transmit forces to drive the cutting section along a desired trajectory for removal of the stem implant, the clearance section including a continuous unitary body that extends laterally away from the longitudinal axis in a partially helical curvature to provide clearance around a neck of the stem implant while the cutting section is being driven along a desired trajectory.

13. The tool of claim 12, wherein the clearance section includes a first portion and a second portion, wherein a distal end of the first portion and a distal end of the second portion converge and connect to the cutting section, and wherein a proximal end of the first portion and the second portion diverge such that the first portion and the second portion form a U-shaped profile.

14. The tool of claim 13, wherein a handle section is disposed on the proximal end of each of the first portion and the second portion, the handle section extending from a proximal portion to a distal portion, the proximal portion of the handle section configured to receive and transmit forces to drive the cutting section along a desired trajectory for removal of the stem implant, and wherein the handle section includes a strike plate.

15. The tool of claim 12, wherein the clearance section includes a first portion and a second portion, wherein a distal end of the first portion and a distal end of a second portion converge and connect to the cutting section, and wherein a proximal end of the first portion and the second portion diverge such that the first portion and the second portion form a V-shaped profile.

16. The tool of claim 15, wherein a handle section is disposed on the proximal end of each of the first portion and the second portion, the handle section extending from a proximal portion to a distal portion, the proximal portion of the handle section configured to receive and transmit forces to drive the cutting section along a desired trajectory for removal of the stem implant, and wherein the handle section includes a strike plate.

17. The tool of claim 12, wherein the clearance section comprises a first aperture configured to provide clearance between the clearance section and the stem implant to prevent engagement between the clearance section and the stem implant.

18. The tool of claim 12, wherein the clearance section comprises a concave profile, the concave profile configured to provide clearance between the clearance section and the stem implant to prevent engagement between the clearance section and the stem implant.

19. A method of removing a stem implant from a femur using the tool of claim 12, the method comprising:

cutting through femur growing into portions of the stem implant using the blade thereby facilitating removal of the stem implant.

20. The method of claim 19, wherein cutting through femur growing into portions of the stem implant using the blade, comprises:

impacting a strike plate disposed on the proximal portion of the clearance section.

* * * * *